US 8,286,467 B2

(12) United States Patent
Fatemi et al.

(10) Patent No.: US 8,286,467 B2
(45) Date of Patent: Oct. 16, 2012

(54) METHOD FOR IMAGING SURFACE ROUGHNESS USING ACOUSTIC EMISSIONS INDUCED BY ULTRASOUND

(75) Inventors: Mostafa Fatemi, Rochester, MN (US); Farid G. Mitri, Rochester, MN (US)

(73) Assignee: MAYO Foundation for Medical Education and Research, Rochester, MN (US)

( * ) Notice: Subject to any disclaimer, the term of this patent is extended or adjusted under 35 U.S.C. 154(b) by 1103 days.

(21) Appl. No.: 12/135,829

(22) Filed: Jun. 9, 2008

(65) Prior Publication Data
US 2009/0114019 A1 May 7, 2009

Related U.S. Application Data

(60) Provisional application No. 60/933,642, filed on Jun. 7, 2007.

(51) Int. Cl.
*G01N 29/14* (2006.01)
*G01N 29/34* (2006.01)
(52) U.S. Cl. ............... 73/105; 73/618; 73/619; 73/643; 73/587
(58) Field of Classification Search .............. 73/104, 73/105, 587, 643, 618, 619
See application file for complete search history.

(56) References Cited

U.S. PATENT DOCUMENTS

| 3,550,075 A * | 12/1970 | Hilchie et al. ............... 367/28 |
| 3,688,569 A * | 9/1972 | Murdoch ..................... 73/105 |
| 4,225,954 A * | 9/1980 | Medwin ...................... 367/118 |
| 4,646,565 A * | 3/1987 | Siegfried .................. 73/152.58 |
| 4,738,139 A * | 4/1988 | Blessing et al. ............... 73/644 |
| 5,214,616 A * | 5/1993 | Terhune et al. ............... 367/99 |
| 5,771,310 A * | 6/1998 | Vannah ....................... 382/154 |
| 5,903,516 A | 5/1999 | Greenleaf et al. |
| 5,921,928 A | 7/1999 | Greenleaf et al. |
| 5,991,239 A | 11/1999 | Fatemi-Booshehri et al. |
| 2006/0272418 A1* | 12/2006 | Maris et al. .................. 73/606 |

* cited by examiner

*Primary Examiner* — Peter Macchiarolo
*Assistant Examiner* — Rose M Miller
(74) *Attorney, Agent, or Firm* — Quarles & Brady, LLP (57) ABSTRACT

A method for measuring variations of the surface of an object using acoustic energy in the audio range is provided. Imaging fine surface roughness on the order of few microns is achievable by using a vibroacoustography technique. This technique provides a method for imaging surface roughness on the basis of an ultrasound radiation force that stimulates acoustic emissions at an ultrasound standing wave field. The present invention may be employed as a tool for the nondestructive inspection and imaging of the surface variations of an object.

32 Claims, 7 Drawing Sheets

METHOD FOR IMAGING SURFACE ROUGHNESS USING ACOUSTIC EMISSIONS INDUCED BY ULTRASOUND

CROSS-REFERENCE TO RELATED APPLICATIONS

This application claims the benefit of U.S. Provisional patent application Ser. No. 60/933,642 filed on Jun. 7, 2007, and entitled "Method For Imaging Surface Roughness Using Acoustic Emissions Induced by Ultrasound", which is herein incorporated by reference.

STATEMENT REGARDING FEDERALLY SPONSORED RESEARCH

This invention was made with government support under Grant No. EB000535 awarded by the National Institute of Biomedical Imaging and Bioengineering. The United States Government has certain rights in this invention.

BACKGROUND OF THE INVENTION

The field of the invention is ultrasound imaging methods and systems. More specifically, the field of the invention is ultrasonic nondestructive techniques for imaging the roughness of a surface.

There are a number of modes in which ultrasound can be used to produce images of objects. The ultrasound transmitter may be placed on one side of the object and the sound transmitted through the object to the ultrasound receiver placed on the other side ("transmission mode"). With transmission mode methods, an image may be produced in which the brightness of each pixel is a function of the amplitude of the ultrasound that reaches the receiver ("attenuation" mode), or the brightness of each pixel is a function of the time required for the sound to reach the receiver ("time-of-flight" or "speed of sound" mode). In the alternative, the receiver may be positioned on the same side of the object as the transmitter and an image may be produced in which the brightness of each pixel is a function of the amplitude or time-of-flight of the ultrasound reflected from the object back to the receiver ("refraction", "backscatter", or "echo" mode).

There are a number of well known backscatter methods for acquiring ultrasound data. In the so-called "A-scan" method, an ultrasound pulse is directed into the object by the transducer and the amplitude of the reflected sound is recorded over a period of time. The amplitude of the echo signal is proportional to the scattering strength of the refractors in the object and the time delay is proportional to the range of the refractors from the transducer. In the so-called "B-scan" method, the transducer transmits a series of ultrasonic pulses as it is scanned across the object along a single axis of motion. The resulting echo signals are recorded as with the A-scan method and either their amplitude or time delay is used to modulate the brightness of pixels on a display. With the B-scan method, enough data are acquired from which an image of the refractors can be reconstructed.

Ultrasonic transducers for medical applications are constructed from one or more piezoelectric elements sandwiched between a pair of electrodes. Such piezoelectric elements are typically constructed of lead zirconate titanate (PZT), polyvinylidene diflouride (PVDF), or PZT ceramic/polymer composite. The electrodes are connected to a voltage source, and when a voltage is applied, the piezoelectric elements change in size at a frequency corresponding to that of the applied voltage. When a voltage pulse is applied, the piezoelectric element emits an ultrasonic wave into the media to which it is coupled at the frequencies contained in the excitation pulse. Conversely, when an ultrasonic wave strikes the piezoelectric element, the element produces a corresponding voltage across its electrodes. Typically, the front of the element is covered with an acoustic matching layer that improves the coupling with the media in which the ultrasonic waves propagate. In addition, a backing material is disposed to the rear of the piezoelectric element to absorb ultrasonic waves that emerge from the back side of the element so that they do not interfere. A number of such ultrasonic transducer constructions are disclosed, for example, in U.S. Pat. Nos. 4,217,684; 4,425,525; 4,441,503; 4,470,305 and 4,569,231.

When used for ultrasound imaging, the transducer typically has a number of piezoelectric elements arranged in an array and driven with separate voltages (apodizing). By controlling the time delay (or phase) and amplitude of the applied voltages, the ultrasonic waves produced by the piezoelectric elements (transmission mode) combine to produce a net ultrasonic wave focused at a selected point. By controlling the time delay and amplitude of the applied voltages, this focal point can be moved in a plane to scan the subject.

The same principles apply when the transducer is employed to receive the reflected sound (receiver mode). That is, the voltages produced at the transducer elements in the array are summed together such that the net signal is indicative of the sound reflected from a single focal point in the subject. As with the transmission mode, this focused reception of the ultrasonic energy is achieved by imparting separate time delay (and/or phase shifts) and gains to the signal from each transducer array element.

This form of ultrasonic imaging is referred to as "phased array sector scanning", or "PASS". Such a scan is comprised of a series of measurements in which the steered ultrasonic wave is transmitted, the system switches to receive mode after a short time interval, and the reflected ultrasonic wave is received and stored. Typically, the transmission and reception are steered in the same direction ($\theta$) during each measurement to acquire data from a series of points along a scan line. The receiver is dynamically focused at a succession of ranges (R) along the scan line as the reflected ultrasonic waves are received. The time required to conduct the entire scan is a function of the time required to make each measurement and the number of measurements required to cover the entire region of interest at the desired resolution and signal-to-noise ratio. For example, a total of 128 scan lines may be acquired over a 90 degree sector, with each scan line being steered in increments of 0.70 degrees. A number of such ultrasonic imaging systems are disclosed, for example, in U.S. Pat. Nos. 4,155,258; 4,155,260; 4,154,113; 4,155,259; 4,180,790; 4,470,303; 4,662,223; 4,669,314 and 4,809,184.

Vibroacoustography is an elasticity modality that vibrates tissue using ultrasound radiation force. The radiation force is generated by focusing two ultrasound beams on the object. These two ultrasound beams have slightly different frequencies and the tissue at the focal point vibrates at an acoustic force frequency equal to the difference, or beat, frequency. The acoustic force frequency can be easily changed. The tissue is scanned in a raster manner and its acoustic emission is detected by a hydrophone. The acquired emission data may be processed to reconstruct an image, which is related to. The details of vibroacoustography are described, for example, in U.S. Pat. Nos. 5,903,516 and 5,991,239.

Ultrasound has found wide usage not only in the field of medical imaging, but also in the field of the nondestructive testing (NDT) of objects for defects such as cracking and corrosion. NDT is employed for many different industrial applications, including testing aerospace construction materials for microstructural cracks, assessing the quality of welds, and determining the presence of cracks in microelectronics.

Coronal scan (C-scan) ultrasound imaging in the frequency range of 0.1-100 MHz is employed in NDT techniques to obtain images of the surface roughness of an object. These methods rely on acquiring ultrasound waves that interact with the surface of the object under investigation. More specifically, these techniques are based on the evaluation of the scattered or reflected ultrasound waves measured by an ultrasonic transducer. While useful for NDT, these conventional ultrasound methods have a number of disadvantages. First, they are unable to image surface roughness of anisotropic materials and thick layered structures. Furthermore, they do not produce high resolution images at audio frequencies, and they require very complex signal processing methods to produce an image.

Scanning acoustic microscopy (SAM) is another NDT method that employs ultrasound, and is one that is used in microelectronics industries. Like the C-scan method, SAM works by directing focused sound from an ultrasonic transducer to a selected point on a test object. Scattering or reflected ultrasound waves are then measured in order to produce an image of the object under examination. The focused ultrasound beam is then moved over the surface of the test object until the entire surface has been assessed. The resolution of the produced image is determined by the frequency of the ultrasound beam. Thus, frequencies in the gigahertz range are often times employed when examining microelectronics so that high resolution images can be produced. While the SAM method provides higher spatial resolution than the C-scan method, it presents a problem of heating, and thus possibly damaging, the object resultant from the high frequency focused ultrasound employed in SAM techniques. Furthermore, the higher frequency ultrasound waves are more likely to be absorbed and attenuated by the object being tested, thus decreasing the efficiency of the imaging process.

SUMMARY OF THE INVENTION

The present invention overcomes the drawbacks of the previous methods for ultrasonic nondestructive testing (NDT) by providing a method that produces images with high spatial resolution while using acoustic energy at lower frequencies. More specifically, the present invention employs vibroacoustography ("VA") for detecting micron-sized surface variations.

One aspect of the invention is designed to provide a method for measuring the variations on the surface of an object by imparting an acoustic force to the object at a selected acoustic force frequency. In one configuration, the acoustic force is produced by employing an ultrasound system, in which an ultrasound transducer is used to emit ultrasound beams at different frequencies. These beams create an amplitude modulated (oscillatory) acoustic force in the region of their intersection beating at the difference frequency (beat frequency) of the ultrasound beams. For example, in one embodiment of the present invention, the beat frequency is in the kilohertz range. As a result of the applied force, the object under examination vibrates according to its viscoelastic properties and emits acoustic energy at a selected acoustic force frequency equal to the beat frequency in a surrounding medium, which includes, for example, water and air.

In another aspect of the invention, an object is scanned by a point-by-point method with at least two intersecting ultrasound beams. As such, acoustic energy is emitted by the object at a selected acoustic force frequency equal to the beat frequency between the at least two beams, which is detected and processed to produce an image indicative of the variations in the surface of the object.

In another aspect of the invention, an object is scanned by a point-by-point method with an amplitude-modulated ultrasound beam. As such, acoustic energy is emitted by the object at a selected acoustic force frequency equal to the modulation frequency of the amplitude modulated beam, which is detected and processed to produce an image indicative of the variations in the surface of the object.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE PREFERRED EMBODIMENT

Figure 1:
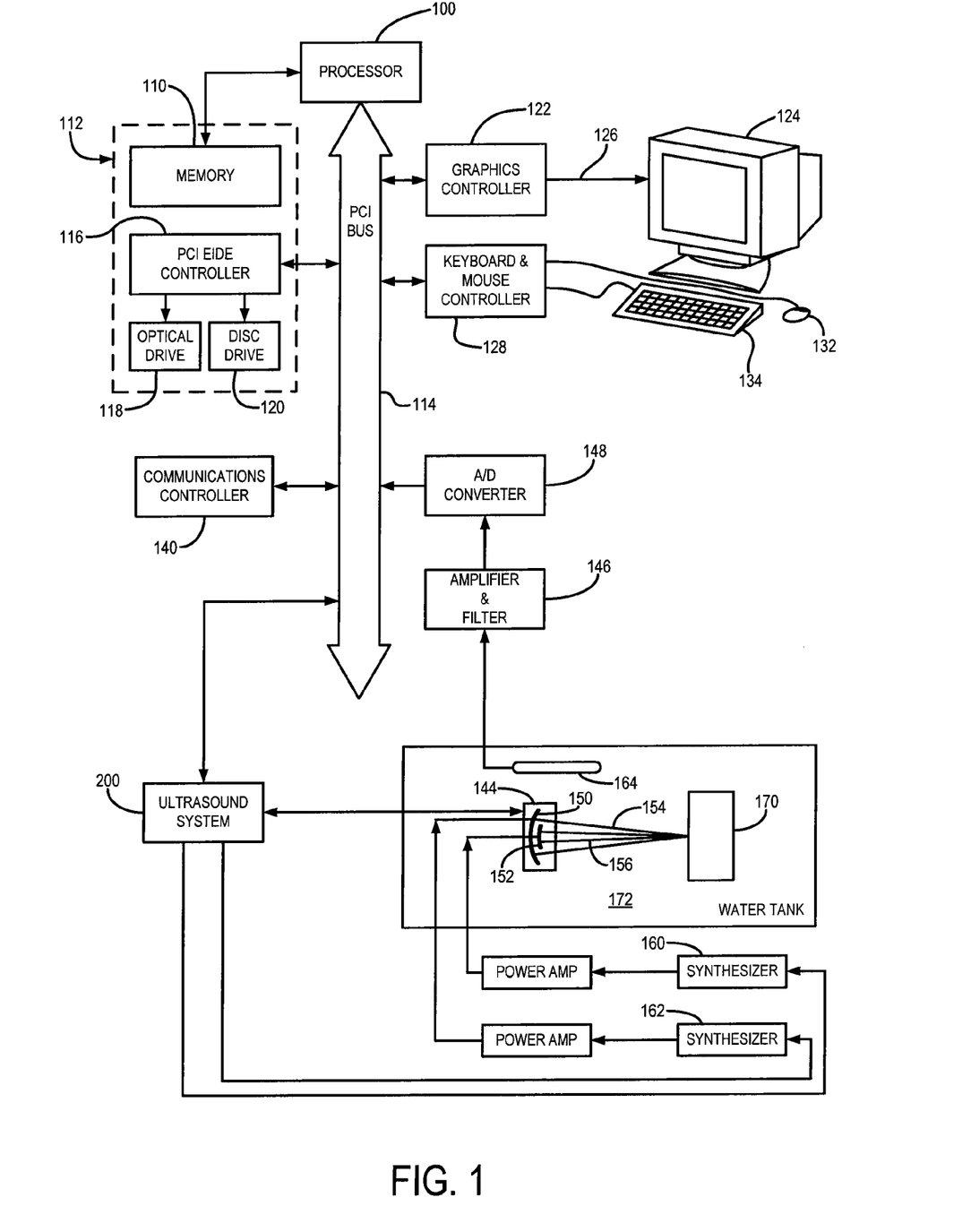
FIG. 1 is a block diagram of a system designed to practice the present invention.

Referring particularly to FIG. 1, the preferred embodiment of the present invention employs an imaging system that includes a workstation. The computer workstation includes a processor 100 which executes program instructions stored in a memory 110 that forms part of a storage system 112. The processor 100 is a commercially available device designed to operate with one of the Microsoft Corporation Windows operating systems. It includes internal memory and I/O control to facilitate system integration and integral memory management circuitry for handling all external memory 110. The processor 100 also includes a PCI bus driver which provides a direct interface with a PCI bus 114.

The PCI bus 114 is an industry standard bus that transfers data between the processor 100 and a number of peripheral controller cards. These include a PCI EIDE controller 116 which provides a high-speed transfer of data to and from an optical drive 118 and a disc drive 120. A graphics controller 122 couples the PCI bus 114 to a monitor 124 through a standard display connection 126, and a keyboard and a mouse controller 128 receives data that is manually input through a keyboard 130 and mouse 132.

The PCI bus 114 also connects to a communications controller 140. The controller 140 connects to an intranet that links the workstation to one or more imaging systems, a department picture archiving and communication system (PACS), or an institution image management system.

The workstation controls the scanning of the surface being imaged by outputting signals to an ultrasound system 200. The ultrasound system is either mechanically or electrically coupled to an ultrasound transducer 144 to either mechanically or electrically control the direction of two, concentric ultrasound beams 154 and 156, as will be described in detail below. The beams 154 and 156 are swept across the surface of an object 170 under test in a raster scan pattern in response to commands output to the ultrasound system 200. While the use of two ultrasound beams 154 and 156 produced by a confocal transducer 144 is preferred, alternatives are possible. One possible variation is to use a single transducer as described in U.S. Pat. No. 5,921,928 to produce the vibroacoustic response. In this embodiment, the ultrasonic transducer produces a single beam which is modulated in amplitude to a chosen frequency equal to twice the frequency of the acoustic emission. In the above embodiment where the difference frequency $\Delta f$ establishes the acoustic emission, an amplitude modulation frequency of the single beam at $2\Delta f$ will result in a similar acoustic emission. Likewise, more than two ultrasound beams may be employed.

In one embodiment, two elements 150 and 152 of the confocal transducer 144 produce two focused beams 154 and 156 that cross each other at their focal points, as described in U.S. Pat. No. 5,991,239. The elements 150 and 152 are driven by respective continuous wave synthesizers 162 and 160 (for example, model HP 33120A waveform generators, Agilent Technologies, Santa Clara, Calif.) at ultrasonic frequencies $f_1$ and $f_2$ that differ by a beat frequency, $\Delta f$. The two focused beams 154 and 156 are aimed at the object 170 which is to be examined, and in response, the target object vibrates, or oscillates, according to its viscoelastic properties and emits an acoustic field at an acoustic force frequency. In the alternative, an amplitude modulated ultrasound beam is employed to produce an acoustic field that oscillates at an acoustic force frequency proportional to the frequency of the amplitude modulation, as described in U.S. Pat. No. 5,921,928. Therefore, when employing two focused beams 154 and 156 that differ by a beat frequency, $\Delta f$, the acoustic force frequency is equal to the beat frequency, $\Delta f$. These elements thus serve as a force generator which oscillates the target object 170 at a prescribed acoustic force frequency. Further in the alternative, more than two ultrasound beams may be employed to produce the acoustic force.

The acoustic field is produced in a medium 172, such as degassed water, and is received by a hydrophone 164, for example, a model ITC-6050C omnidirectional hydrophone (International Transducer Corp., Santa Barbara, Calif.). While the use of hydrophone as described is a practical way of detecting the vibration of the object, other types of sensors may be used to detect object vibration. One possible method is to use an accelerometer attached to the object to detect vibration. Another choice would be to use an optical interferometer such as a laser vibrometer, to detect object vibration. In response to the acoustic field, the hydrophone produces a signal that is applied to an amplifier and band pass filter circuit 146, for example, a model SR650 elliptical filter (Stanford Research Systems, Sunnyvale, Calif.), which is centered on the acoustic force frequency. In one embodiment, the acoustic force frequency is equal to the beat frequency produced between two focused ultrasound beams 154 and 156 having different frequencies. In the alternative, and as described above, the acoustic force frequency is proportional to the modulation frequency of an amplitude modulated ultrasound beam. The filtered and amplified signal is then applied to a 12 bits/sample analog-to-digital converter 148 at a rate sufficiently higher than the Nyquist rate and input to the workstation.

The workstation is programmed to coordinate the scan and process the digitized acoustic force frequency signals to produce an image. The programmed processor 100 in the workstation calculates the mean amplitude (or the standard deviation) of the digitized acoustic force signal, then stores this value in an image array at a location corresponding to the beam intersection position. Processor 100 also controls other parts of the system to carry out the scan process. It directs the beams 154 and 156 such that their intersect region raster scans the object 170 in the x-y plane. Processor 100 also provides the trigger signals needed to synchronize the scanning and digitization function. The resulting acoustic force signal image produced after a complete raster scan may be enhanced using known image enhancement methods and/or displayed on a monitor 124. A two-dimensional image is thus produced in which the gray scale intensity of each pixel indicates the acoustic level produced at the acoustic force frequency.

As described in U.S. Pat. No. 5,903,516 a force is generated at the intersection of the two ultrasound beams 154 and 156 at an acoustic force frequency equal to the beat frequency $\Delta f$. As a result of this applied force, the surface under examination vibrates according to its viscoelastic properties and emits an acoustic field in the surrounding medium. By scanning the object point-by-point, the acoustic emission resulting from object vibration is detected by the hydrophone 164 and processed to construct the image as described above. When the surface is not totally absorptive, however, ultrasound waves are reflected back and forth multiple times between the object 170 and the transducer 144. Depending on the object-to-transducer distance and the ultrasound wavelength, these waves interact either constructively or destructively. As a result, an ultrasound standing (or stationary) wave field is established. This stationary field affects the radiation force exerted on the object 170 as well as the resulting acoustic emitted field picked up by hydrophone 164 in a way that it rapidly fluctuates versus distance or frequency. The rate of change in the acoustic emission pressure field depends on the number of reflections that occur between the object and the transducer and the ultrasound wavelength. If a planar object is moved along the beam axis from a maximum to a minimum of the standing wave, the acoustic emission, and hence image brightness, decreases. Likewise, roughness variations (within the range corresponding to the distance between a maximum and a minimum in the standing wave) on a surface of a plane object can be detected based on the same variations of the acoustic emission amplitude. The spatial resolution achievable by the present invention depends on the wavelengths of the ultrasound beams 154 and 156, as has the form:

$$\delta = \frac{\lambda}{4 \cdot n} = \left(\frac{1}{4 \cdot n}\right) \cdot \frac{(\lambda_1 + \lambda_2)}{2}, \quad (1)$$

Where δ is the distance between a maximum and minimum of the acoustic emission standing wave, $\tilde{\lambda}$ is the mean ultrasound wavelength, $\lambda_1$ is the wavelength of the ultrasound beam 154, $\lambda_2$ is the wavelength of the ultrasound beam 156, and n is number of reflections that occur between the transducer 144 and the object 170. The distance δ defines the resolution of the imaging system. That is, the present invention may be employed to image surface variations not in excess of the distance, δ. For example, if $\tilde{\lambda}$=748 µm and the number of reflections between the transducer 144 and the object 170 are held to n=2, the present invention can be employed to image surface variations within a range of $\tilde{\lambda}/8$=93.5 µm.

A standing wave is established between the ultrasound transducer 144 and the surface of the target object 170. When the target object 170 is not totally absorptive, ultrasound waves are reflected back and forth multiple times between the target object 170 and the transducer 144. Depending on the object-to-transducer distance and the ultrasound wavelength, these waves interact constructively or destructively. As a result, an ultrasound standing (or stationary) wave field is established. This stationary field affects the acoustic force exerted on the object as well as the resulting acoustic energy, or "acoustic emission", in a way that it rapidly fluctuates versus distance or frequency. The rate of change in the acoustic emission depends on the number of reflections that occur between the object and the transducer and the ultrasound wavelength. The present invention utilizes this ultrasound standing wave phenomenon to detect roughness variations within the micrometer range on the surface of the object 170.

Figure 2:
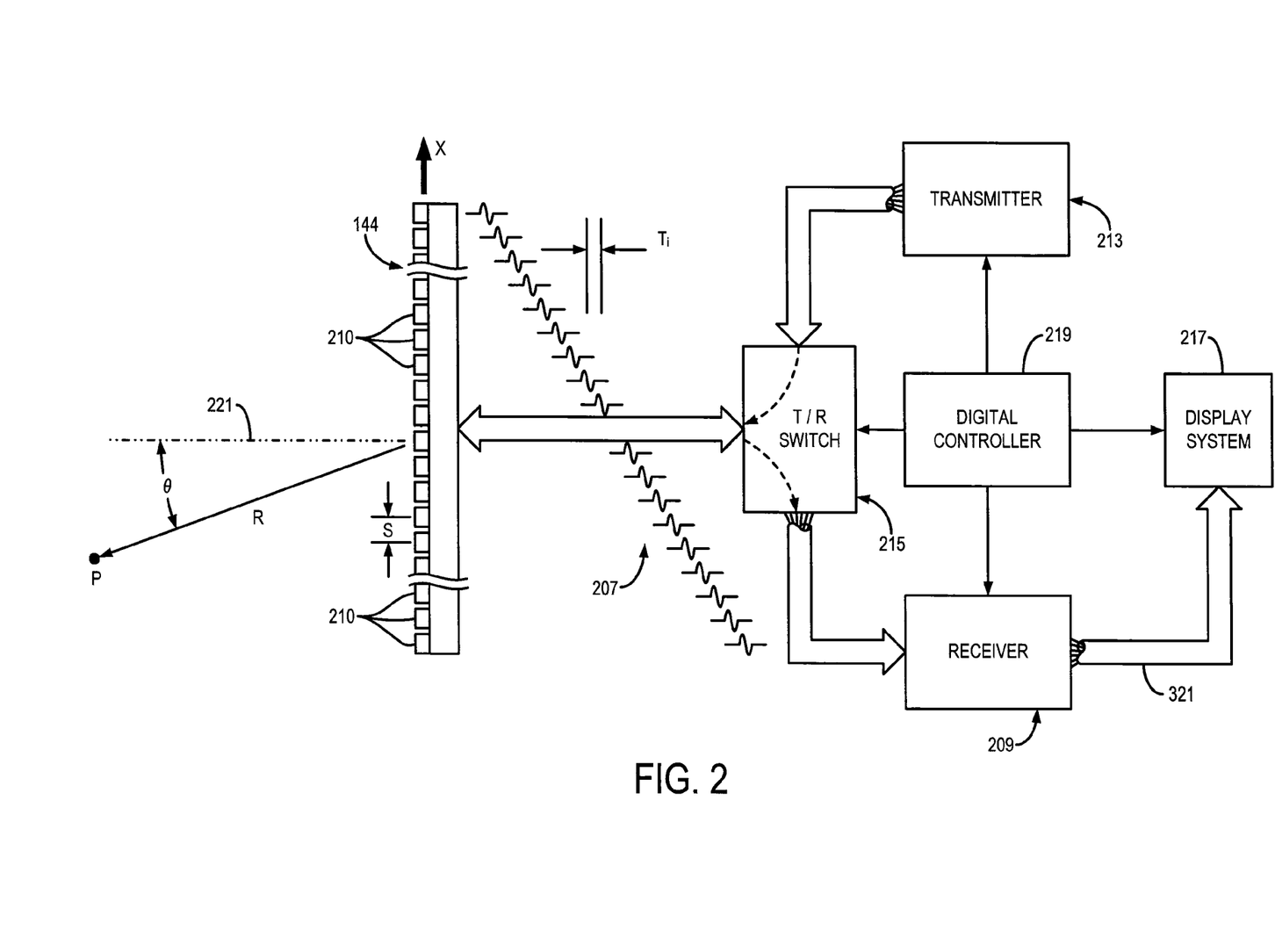
FIG. 2 is a block diagram of an ultrasonic imaging system that forms a part of the system of FIG. 1.

Referring particularly to FIG. 2, one embodiment of an ultrasound system employed when practicing the present invention includes a transducer array 144. The transducer array 144 includes a plurality of separately driven elements 210 which each produce a burst of ultrasonic energy when energized by a pulse produced by a transmitter 213. The ultrasonic energy reflected back to the transducer array 144 from the subject under study is converted to an electrical signal by each transducer element 210 and applied separately to a receiver 209 through a set of switches 215. The transmitter 213, receiver 209 and the switches 215 are operated under the control of a digital controller 219 responsive to the commands input by the human operator. A complete scan is performed by acquiring a series of echoes in which the switches 215 are set to their transmit position, the transmitter 213 is gated on momentarily to energize each transducer element 210, the switches 215 are then set to their receive position, and the subsequent echo signals produced by each transducer element 210 are applied to the receiver 209. The separate echo signals from each transducer element 210 are combined in the receiver 209 to produce a single echo signal which is employed to produce a line in an image on a display system 217, which can include the monitor 124 of the workstation shown in FIG. 1.

The transmitter 213 drives the transducer array 144 such that the ultrasonic energy produced is directed, or steered, in a beam. A B-scan can therefore be performed by moving this beam through a set of angles from point-to-point rather than physically moving the transducer array 144. To accomplish this the transmitter 213 imparts a time delay ($T_i$) to the respective pulses 207 that are applied to successive transducer elements 210. If the time delay is zero ($T_i$=0), all the transducer elements 210 are energized simultaneously and the resulting ultrasonic beam is directed along an axis 221 normal to the transducer face and originating from the center of the transducer array 144. As the time delay ($T_i$) is increased, the ultrasonic beam is directed downward from the central axis 221 by an angle θ.

A sector scan is performed by progressively changing the time delays $T_i$ in successive excitations. The angle θ is thus changed in increments to steer the transmitted beam in a succession of directions. When the direction of the beam is above the central axis 221, the timing of the pulses 207 is reversed.

Referring still to FIG. 2, the echo signals produced by each burst of ultrasonic energy emanate from reflecting objects located at successive positions (R) along the ultrasonic beam. These are sensed separately by each segment 210 of the transducer array 144 and a sample of the magnitude of the echo signal at a particular point in time represents the amount of reflection occurring at a specific range (R). Due to the differences in the propagation paths between a focal point P and each transducer element 210, however, these echo signals will not occur simultaneously and their amplitudes will not be equal. The function of the receiver 209 is to amplify and demodulate these separate echo signals, impart the proper time delay to each and sum them together to provide a single echo signal which accurately indicates the total ultrasonic energy reflected from each focal point P located at range R along the ultrasonic beam oriented at the angle θ.

To simultaneously sum the electrical signals produced by the echoes from each transducer element 210, time delays are introduced into each separate transducer element channel of the receiver 209. In the case of the linear array 144, the delay introduced in each channel may be divided into two components, one component is referred to as a beam steering time delay, and the other component is referred to as a beam focusing time delay. The beam steering and beam focusing time delays for reception are precisely the same delays ($T_i$) as the transmission delays described above. However, the focusing time delay component introduced into each receiver channel is continuously changing during reception of the echo to provide dynamic focusing of the received beam at the range R from which the echo signal emanates.

Under the direction of the digital controller 219, the receiver 209 provides delays during the scan such that the steering of the receiver 209 tracks with the direction of the beam steered by the transmitter 213 and it samples the echo signals at a succession of ranges and provides the proper delays to dynamically focus at points P along the beam. Thus, each emission of an ultrasonic pulse results in the acquisition of a series of data points which represent the amount of reflected sound from a corresponding series of points P located along the ultrasonic beam.

The display system 217 receives the series of data points produced by the receiver 209 and converts the data to a form producing the desired image. For example, if an A-scan is desired, the magnitude of the series of data points is merely graphed as a function of time. If a B-scan is desired, each data point in the series is used to control the brightness of a pixel in the image, and a scan comprised of a series of measurements at successive steering angles (θ) is performed to provide the data necessary for display of an image.

Figure 3:
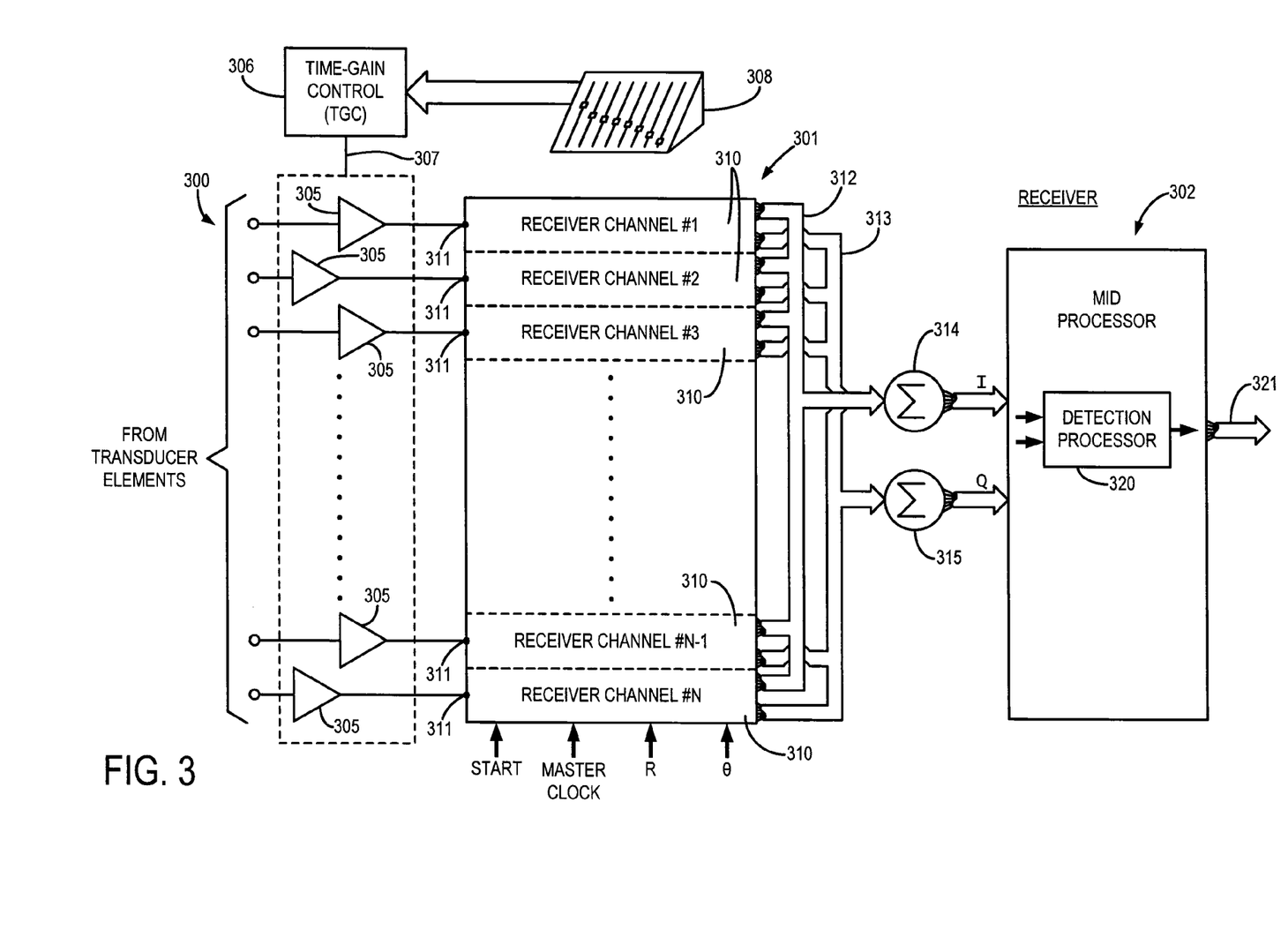
FIG. 3 is a block diagram of a receiver that forms part of the system of FIG. 2.

Referring particularly to FIG. 3, the receiver 209 includes three sections: a time-gain control section 300, a beam forming section 301, and a mid processor 302. The time-gain control section 300 includes an amplifier 305 for each of the N=128 receiver channels and a time-gain control circuit 306. The input of each amplifier 305 is connected to a respective one of the transducer elements 210 to receive and amplify the echo signal which it receives. The amount of amplification provided by the amplifiers 305 is controlled through a control line 307 that is driven by the time-gain control circuit 306. As is well known in the art, as the range of the echo signal increases, its amplitude is diminished. As a result, unless the echo signal emanating from more distant reflectors is amplified more than the echo signal from nearby reflectors, the brightness of the image diminishes rapidly as a function of range (R). This amplification is controlled by the operator who manually sets TGC linear potentiometers 308 to values which provide a relatively uniform brightness over the entire range of the sector scan. The time interval over which the echo signal is acquired determines the range from which it emanates, and this time interval is divided into by the TGC control circuit 306. The settings of the potentiometers are employed to set the gain of the amplifiers 305 during each of the respective time intervals so that the echo signal is amplified in ever increasing amounts over the acquisition time interval.

The beam forming section 301 of the receiver 209 includes N=128 separate receiver channels 310. Each receiver channel 310 receives the analog echo signal from one of the TGC amplifiers 305 at an input 311, and it produces a stream of digitized output values on an I bus 312 and a Q bus 313. Each of these I and Q values represents a sample of the echo signal envelope at a specific range (R). These samples have been delayed in the manner described above such that when they are summed at summing points 314 and 315 with the I and Q samples from each of the other receiver channels 310, they indicate the magnitude and phase of the echo signal reflected from a point P located at range R on the steered beam ($\theta$).

For a more detailed description of the receiver 209, reference is made to U.S. Pat. No. 4,983,970 which issued on Jan. 8, 1991 and is entitled "Method And Apparatus for Digital Phase Array Imaging", and which is incorporated herein by reference.

Referring still to FIG. 3, the mid processor section 302 receives the beam samples from the summing points 314 and 315. The I and Q values of each beam sample is a 16-bit digital number which represents the in-phase and quadrature components of the magnitude of the reflected sound from a point (R, $\theta$). The mid processor 302 can perform a variety of calculations on these beam samples, where choice is determined by the type of image to be reconstructed.

For example, a conventional ultrasound image may be produced by a detection processor 320 which calculates the magnitude of the echo signal from its I and Q components:

$$M=\sqrt{I^2+Q^2}.$$

The resulting magnitude values output at 321 to the display system 217 result in an image in which the magnitude of the reflected echo at each image pixel is indicated.

Figure 4:
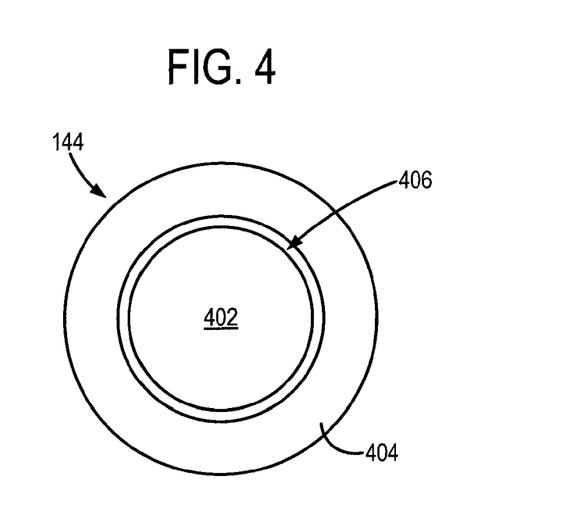
FIG. 4 is a plane view of a first embodiment of an ultrasonic transducer used in the system of FIG. 1.
Figure 5:
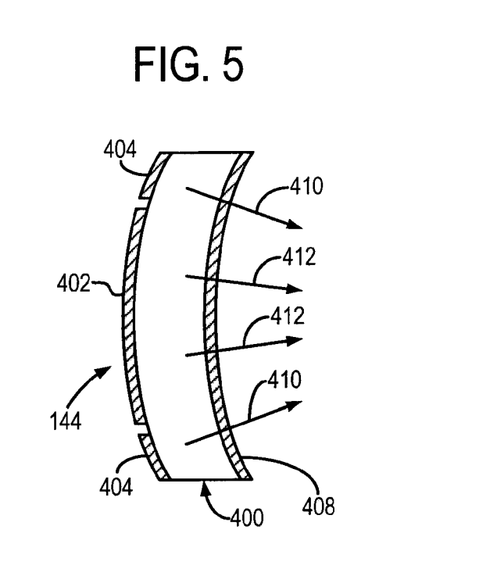
FIG. 5 is a view in cross-section of one configuration of an ultrasonic transducer used in the system of FIG. 1.

Referring particularly to FIGS. 4 and 5, a first preferred embodiment of the transducer 144 includes a piezoelectric base 400 formed from a piezoelectric material such as lead zirconate titanate, which is well known in the art as "PZT". The piezoelectric base 400 has a circular perimeter and a thickness which is determined by the speed of sound in the piezoelectric material and the desired center frequency of the emitted ultrasound.

Disposed on the back surface of the piezoelectric base 400 are two active electrodes 402 and 404. The electrode 402 is a conductive metal layer which is circular in shape. The second active electrode 404 is also a conductive metal layer and it is annular in shape and disposed concentrically around the center electrode 402. The transducer 144 has a diameter of 45 mm and the two active electrodes 402 and 404 have substantially equal surface areas. A single ground electrode 408 is formed over the entire front surface of the piezoelectric base 400 and the entire structure is concave in shape to focus the two ultrasonic beams 154 and 156, indicated by arrows 410 and 412, at a focal point located a distance of 70 mm from the electrodes 402 and 404.

The two active electrodes 402 and 404 are separately driven and form, along with the piezoelectric base 400 and ground electrode 408, the two separate transducer elements 150 and 152. A lead wire (not shown) connects each active electrode 402 and 404 to a separate power amplifier described below and a similar lead wire connects the common ground electrode to both power amplifiers. These two separate transducer elements produce the two beams 154 and 156 which share the same focal point. This common focal point can be moved, or scanned, by physically moving the structure 144 to point its front surface at the surface being scanned. The acoustic force produced at the common focal point as described below, can thus be scanned over the object 170 by moving this single, confocal structure 144.

Figure 6:
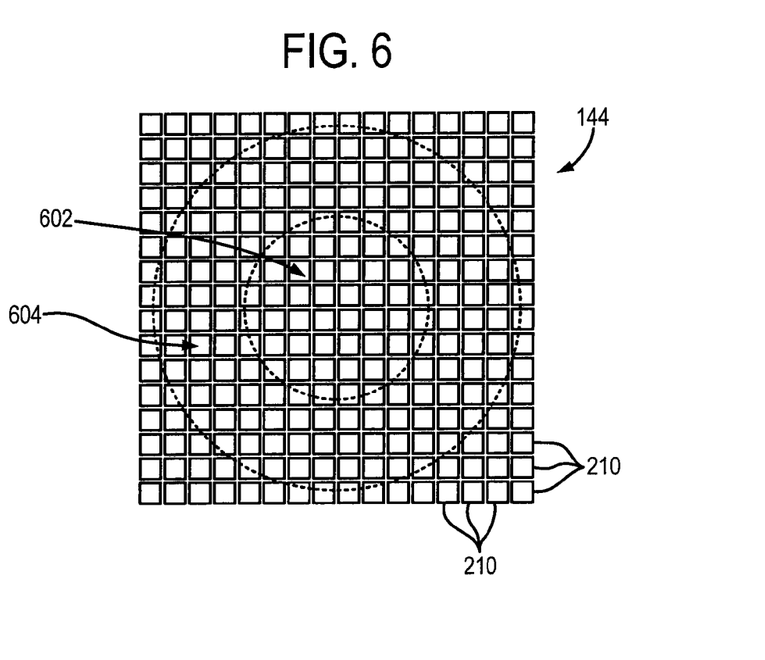
FIG. 6 is a plane view of another configuration of an ultrasonic transducer used in the system of FIG. 1.

Another embodiment of the ultrasonic transducer 144 is shown in FIG. 6. It is similar to the first embodiment expect it is not concave, and the two active electrodes 402 and 404 on its back surface are formed by two dimensional arrays of sub-elements. A two dimensional array consisting of a rectangular grid of M-by-N sub-elements 210, are grouped to form a first element 602 which is substantially circular in shape and an annular-shaped second element 604 which surrounds the first element 602. The sub-elements 210 in the first element 602 are driven at one frequency ($f_1$) and the sub-elements 210 in the second element 604 are driven at a second frequency ($f_2$). The phase and amplitude of the sub-elements 210 in each group 602 and 604 are chosen to form two confocal beams 154 and 156 that converge at the same focal point. An advantage of this method is that the phase of the voltages applied to sub-elements 210 can be changed electronically at high speed, such that the resulting confocal beams 154 and 156 of the array can scan the region of interest in one, two, or three dimensions. Construction methods for two dimensional arrays are well known to those skilled in the art, as described, for example, by Turnbull, D. H.; Foster, F. S.; Fabrication and Characterization of Transducer Elements in Two-Dimensional Arrays for Medical Ultrasound Imaging, IEEE Trans. Ultrason. Ferroelectr. Freq. Control (USA), Vol. 39, No. 4, pp. 464-75, 22 refs. July 1992. For a detailed description of the confocal transducer 144, reference is made to U.S. Pat. No. 5,991,239 which is incorporated herein by reference.

Figure 7:
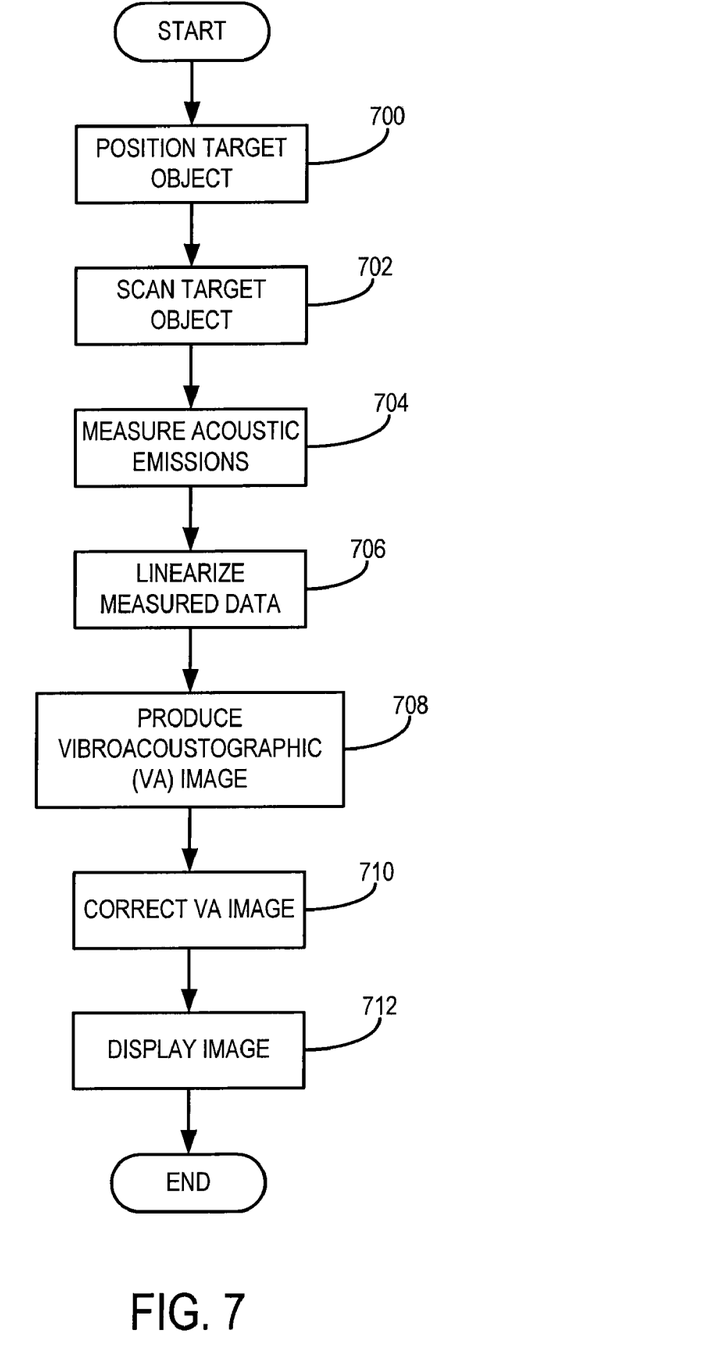
FIG. 7 is a flowchart setting forth the steps of a method employed when practicing the present invention.

Referring particularly to FIG. 7, the steps of a method for practicing the present invention are shown in a flowchart diagram. The method begins at step 700 where the target object 170 is placed in the medium 172 and positioned so that the focal point of the two ultrasound beams 154 and 156 lies substantially on the surface of the target object 170. In one embodiment, the medium 172 is degassed water; however, the medium 172 may also include, for example, air. If the latter is the case, the hydrophone 164 is replaced with a microphone. After the target object 170 has been positioned, the scanning process begins, as indicated at step 702. Starting from a point on the surface of the target object selected by an operator, the intersect region of the ultrasound beams 154 and 156 is scanned along the surface of the target object 170 in a raster pattern. For example, the frequency of the first ultrasound beam 154 is set to 2 MHz and the frequency of the second ultrasound beam 156 is selected such that a beat frequency of 9.9 kHz is produced when the two ultrasound beams 154 and 156 interact. It should be appreciated by those skilled in the art that frequencies of the ultrasound beams 154 and 156 are chosen depending on the desired spatial resolution in accordance with equation 1 above. At each point the hydrophone 164 detects the acoustic emission field produced by the vibrating object, as indicated at step 704.

The relation between the target object 170 surface-to-transducer 144 distance, which is indicative of the surface roughness, and the relative acoustic emission amplitude is not linear. Therefore, in order to make this relation linear, the acoustic emission signal is amplified by the inverse of a calibration signal, as indicated at step 706. The calibration signal is produced by first positioning the transducer 144 in spaced relation from the target object 170 such that the focal point of the two ultrasound beams 154 and 156 intersect at a preselected distance, D, behind the target object. The transducer 144 is then incrementally moved away from the target object 170 until the intersecting focal points of the two ultrasound beams 154 and 156 lie the preselected distance, D, in front of the target object. In a preferred embodiment, the transducer is moved in increments of 5 μm.

An image indicative of the surface variations of the target object 170 is then produced in step 708. It is possible to produce such an image because surface roughness of the target object 170 produces changes in the acoustic emission field as the intersect region of the ultrasound beams 154 and 156 is moved across the surface of the target object 170. When the standing wave produced by the interaction of the two ultrasound beams 154 and 156 is at a maximum, the corresponding image voxel in a produced grayscale image is substantially white voxel. Likewise, when the standing wave of the acoustic emission field is at a minimum, the corresponding image voxel in a grayscale image is substantially black. As the standing wave produced by the two ultrasound beams 154 and 156 changes in response to surface variations, the acoustic emission field also changes. An image of the surface variation of the target object 170 is thus produced by associating the measured amplitudes of the acoustic emission field with a given image voxel intensity.

Not all objects will have a uniform reflection coefficient across their entire surface, therefore, a correction for variations in the surface reflection coefficient is performed at step 710. In a preferred embodiment, the reflection coefficient at each measurement point on the surface of the object 170 is determined and employed to remove errors in the measured data. One method of acquiring the reflection coefficients across the surface of the object 170 is to estimate the reflection coefficient at each measurement point using pulse-echo ultrasound; however, it will appreciated by those skilled in the art that other methods for determining a reflection coefficient exist. The image produced from data acquired using a pulse-echo method is proportional to the pressure reflection coefficient, $r_P$, at each measured point. The image of the surface variations of the object produced in step 708, however, is proportional to the intensity reflection coefficient, $R_I$. Because the pressure and intensity reflection coefficients have a simple relationship, namely:

$$R_I = r_P^2,$$

The image produced in step 708 can be corrected by performing a voxel-wise division of the surface variation image by the square of the pulse-echo image. The resulting image is thus corrected for any variations in the reflection coefficient of the target object 170. As indicated in step 712, the corrected image is then displayed on the display system 217 or can be alternatively stored in the storage system 112 for later viewing or further processing.

Figure 8:
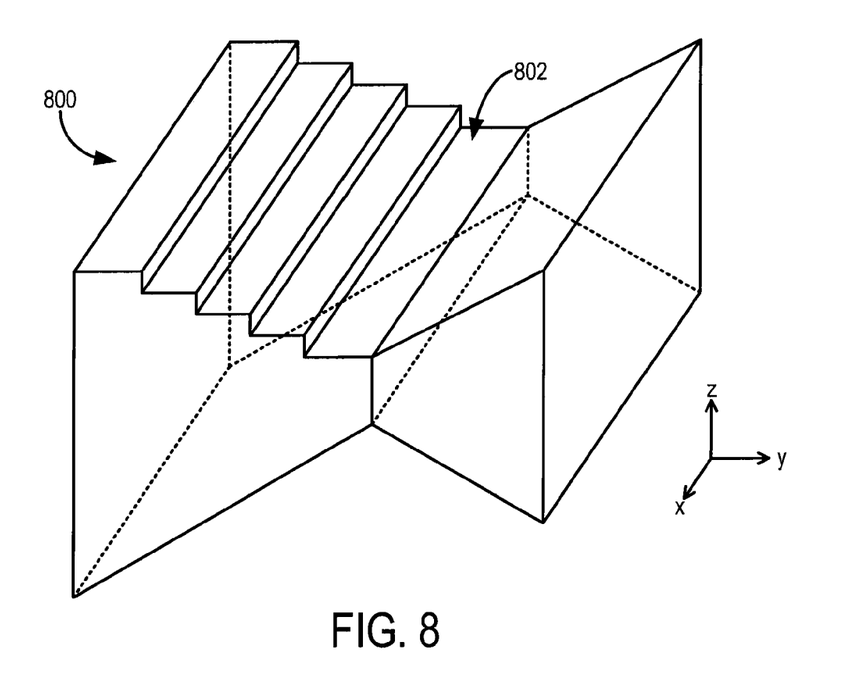
FIG. 8 is a perspective view of an example test object imaged when practicing the present invention.

An illustrative example of the method according to the present invention is presented herein with reference to FIGS. 8, 9, and 10A-C. Referring first to FIG. 8, a test object 800 made of acrylic material is designed in such a way that its top surface includes one side having four steps each 20 μm height, a flat area 802 in its middle part, and a ramp with 30 degrees of inclination on the other side. The bottom surface is shaped as two sloping surfaces to deflect an ultrasound beam and prevent possible reverberation. The test object 800 is immersed in a tank containing a medium 172. In the present example, the medium 172 is degassed water. The test object 800 is placed at the focal point of the ultrasound beams 154 and 156. Acoustic absorbers, in the shape of rubber plates (50×25 cm$^2$) with wedges, are attached to the walls of the tank to minimize low frequency reverberations inside the tank.

Figure 9:
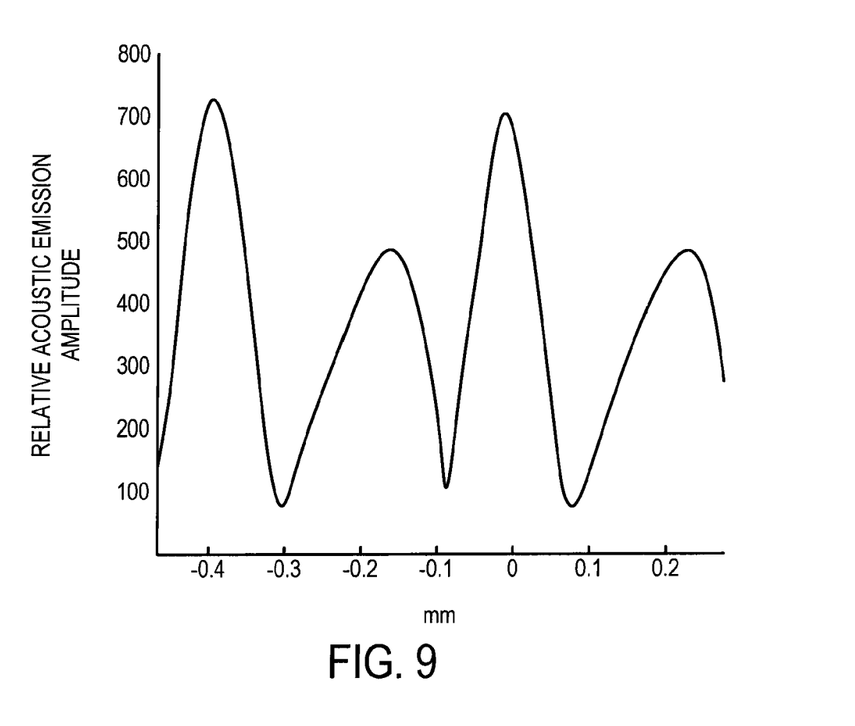
FIG. 9 is a graph of the relative amplitude of acoustic emissions measured as a transducer moves toward the example object of FIG. 8.

A calibration scan is performed by positioning the test object 800 normal to the ultrasound beams 154 and 156 and such that they are focused at the flat area 802 in the middle of the object. The frequency of the first ultrasound beam 154 is set to 2 MHz and the frequency of the second ultrasound beam 156 is set so that a beat frequency, Δf, of 9.9 kHz is produced. The acrylic test object 800 is slowly moved toward the transducer along the beam axis in increments of 5 μm/point, starting at 0.48 mm before the focal point to 0.48 beyond the focal point. While the test object 800 is spanning a distance of 0.96 mm, the acoustic emission signal is recorded. FIG. 9 shows the amplitude of the resulting acoustic emission versus the axial distance. The 0 mm position corresponds to the center of the focal spot lying substantially on the surface of the test object 800. As described above, this calibration scan is employed to linearize the measured signal data.

Figure 10A:
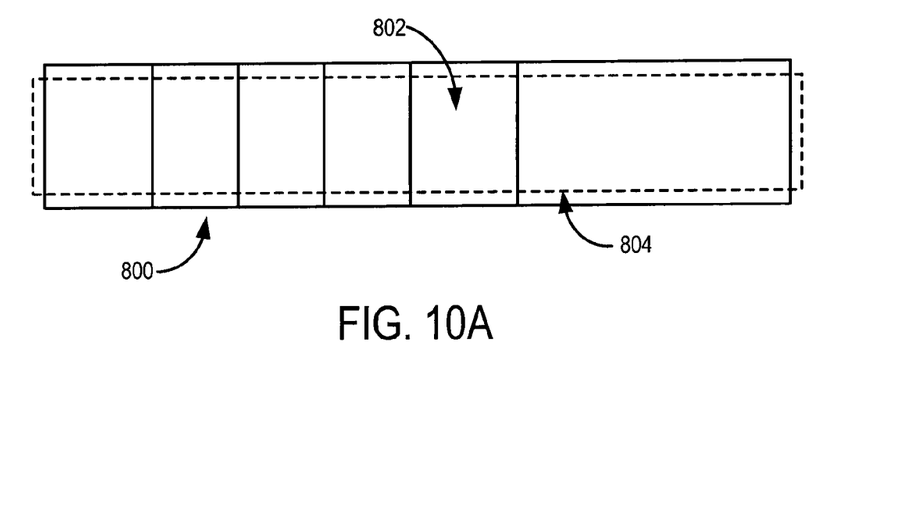
FIG. 10A is a top view of the example test object of FIG. 8 that further defines an imaging area of the test object's surface.
Figure 10B:
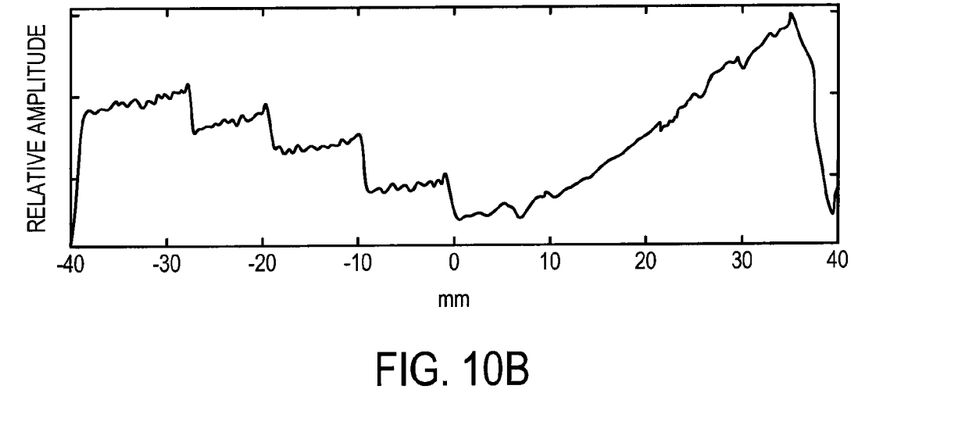
FIG. 10B is a single-line profile of an image of the object of FIG. 8 produced by the present invention.
Figure 10C:
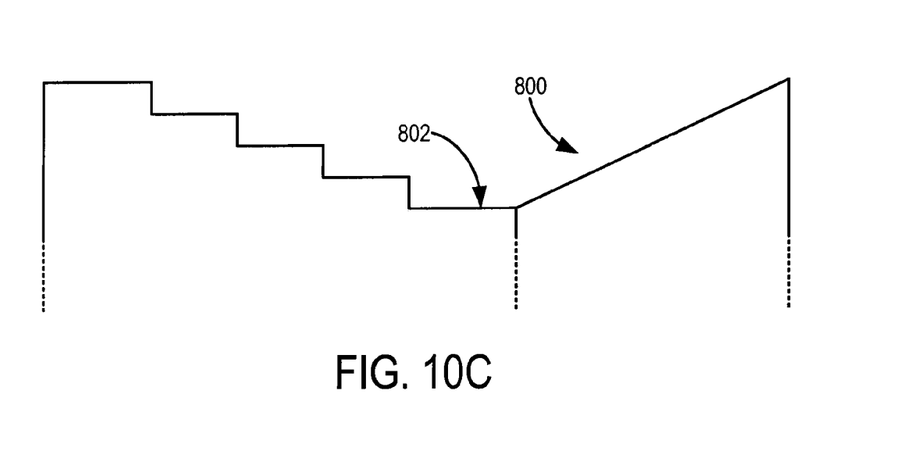
FIG. 10C is a view in cross-section of the test object of FIG. 8 that corresponds to the single-line profile of FIG. 10B.

After performing the calibration scan, the object 800 is positioned such that its highest step is at its original position, that is as the 0 mm position. A top view of the test object 800 is shown in FIG. 10A. Shown in FIG. 10A is an imaging area 804 of 12×80 mm$^2$, which is scanned in increments of 0.25 mm in a raster pattern at the beat frequency, Δf. As described above, the acoustic emission amplitude is recorded while the ultrasound beams 154 and 156 scan the surface of the test object 800. The resultant vibroacoustographic image is indicative of the surface variations present on the test object 800. FIG. 10B shows a one-line profile along the center of such an image, while the corresponding view in cross-section of the test object 800 is shown in FIG. 10C. It can be seen in FIG. 10B that small surface variations of 20 μm height are well identified in addition to the ramp on the right hand side of the test object 800. Each 20 μm step is related to an approximate relative amplitude variation of 27%. Moreover, some peaks in the acoustic emission amplitude tend to appear at the end of each step. These peaks are related to the sidelobes of the transducer's point spread function (PSF). The relative amplitude of these edge peaks varies at the end of each step by approximately 13%, which is equal to the amplitude ratio between the side and central lobes of the PSF.

In addition to producing an image of the surface of an object 170, the present invention may alternatively be employed to produce a one-dimensional profile of the surface of the object under examination similar to the one shown in FIG. 10B. This is achieved by moving the ultrasound transducer 144 over the surface of the object 170 along a contour on the surface. The contour may include, for example, a straight line and a curved arc.

The present invention has been described in terms of one or more preferred embodiments, and it should be appreciated that many equivalents, alternatives, variations, and modifications, aside from those expressly stated, are possible and within the scope of the invention. For example, the present invention can be employed to produce a three-dimensional image of the surface variations over a three-dimensional surface of an object. Also, the ultrasound system employed by the present invention can be operated, for example, to produce a B-mode image of the object. An image of the surface variations of the object can thus be displayed as an overlay on the B-mode image. Furthermore, instead of moving the focused ultrasound energy over the surface of the object under examination, the object itself can equivalently be moved with respect to the ultrasound energy.

The invention claimed is:

1. A method for producing an image indicative of variations of a surface of an object, the steps comprising:
    a) positioning an ultrasonic transducer in spaced relationship over the surface of an object;
    b) operating the ultrasonic transducer to apply an acoustic force to the surface at a selected acoustic force frequency;
    c) sensing an acoustic emission field produced by the object in response to the applied acoustic force;
    d) repeating steps b) and c) while moving the ultrasonic transducer over the surface of the object;
    e) providing a calibration signal that indicates standing waves between the surface of the object and the ultrasonic transducer for a plurality of different distances between the surface of the object and the ultrasonic transducer; and
    f) producing an image indicative of variations of the surface of the object using the acoustic emission fields sensed in steps c) and d) and using the calibration signal provided in step e).

2. The method as recited in claim 1 in which step b) includes:
    focusing an ultrasonic energy produced by the ultrasonic transducer; and
    moving the focused ultrasonic energy over the surface of the object to measure the spacing between the surface of the object and the ultrasonic transducer at different locations thereon.

3. The method as recited in claim 2 in which the ultrasonic transducer is comprised of an array of transducer elements and the focused ultrasonic energy is moved electronically.

4. The method as recited in claim 1 in which the ultrasonic transducer is moved in a raster scan of the surface.

5. The method as recited in claim 1 in which the ultrasonic transducer produces two ultrasonic beams that differ in frequency by a beat frequency.

6. The method as recited in claim 5 in which the selected acoustic force frequency is equal to the beat frequency.

7. The method as recited in claim 1 in which the ultrasonic transducer produces a single, amplitude-modulated beam in which the frequency of the amplitude modulation results in a modulation frequency.

8. The method as recited in claim 7 in which the selected acoustic force frequency is proportional to the modulation frequency.

9. The method as recited in claim 1 further including:
    g) estimating a surface reflection coefficient at locations on the surface; and
    h) correcting the image produced in step f) for variations in the surface reflection coefficient over the surface.

10. The method as recited in claim 9 in which step g) includes producing an image indicative of a pressure reflection coefficient at locations on the surface.

11. The method as recited in claim 10 in which step h) includes dividing an image voxel value of the image produced in step f) by a square of an image voxel value of a corresponding voxel in the image produced in step g).

12. The method as recited in claim 1 which step b) includes:
    focusing an ultrasonic energy produced by the ultrasonic transducer; and
    moving the object with respect to the focused ultrasonic energy to measure the spacing between the surface of the object and the ultrasonic transducer at different locations thereon.

13. The method as recited in claim 1 in which the acoustic energy is sensed in step c) by a hydrophone.

14. The method as recited in claim 1 in which the acoustic energy is sensed in step c) by a laser vibrometer.

15. The method as recited in claim 1 in which step a) includes positioning at least a second ultrasonic transducer in spaced relationship over the surface and step b) includes operating the at least second ultrasonic transducer to apply an acoustic force to the surface at the selected acoustic force frequency.

16. The method as recited in claim 15 which step b) includes:
    focusing a plurality of ultrasonic energies produced by the ultrasonic transducers at a common focal point on the surface of the object; and
    moving the focused ultrasonic energies over the surface of the object to measure the spacing between the surface of the object and the ultrasonic transducers at different locations thereon.

17. The method as recited in claim 1 in which step e) includes
    i) positioning the ultrasonic transducer in spaced relationship over the surface of the object such that a focal point of the ultrasonic transducer is positioned at a selected distance below the surface of the object;
    ii) operating the ultrasonic transducer to apply an acoustic force to the focal point at a selected acoustic force frequency;
    iii) sensing an acoustic emission field produced by the object in response to the acoustic force applied in step ii);
    iv) repeating steps i)-iii) while incrementally moving the focal point of the ultrasonic transducer along a direction perpendicular to the surface of the object until the focal point is positioned at the selected distance above the surface of the object; and
    v) storing the acoustic emission fields sensed in step iii) as the calibration signal.

18. The method as recited in claim 1 in which step f) includes amplifying the acoustic emission fields sensed in step c) by an inverse of the calibration signal provided in step e).

19. A method for measuring variations of a surface of an object, the steps comprising:
    a) positioning an ultrasonic transducer in spaced relationship over the surface of an object;
    b) operating the ultrasonic transducer to apply an acoustic force to the object at a selected acoustic force frequency;
    c) sensing an acoustic emission field produced by the object in response to the applied acoustic force;
    d) providing a calibration signal that relates a distance of the ultrasonic transducer from the surface of the object to standing waves produced between the ultrasonic transducer and the surface of the object; and
    e) producing a signal having an amplitude indicative of the spacing between the surface of the object and the ultrasonic transducer using the acoustic emission field sensed in step c) and the calibration signal provided in step d).

20. The method as recited in claim 19 which includes:
    focusing an ultrasonic energy produced by the ultrasonic transducer; and moving the focused ultrasonic energy over the surface of the object to measure the spacing at different locations thereon.

21. The method as recited in claim 20 in which the motion is a linear scan along a contour on the surface and a one-dimensional profile of the surface of the object along said contour is produced.

22. The method as recited in claim 20 in which the motion is a raster scan of the surface and an image is produced from the signals produced in step d).

23. The method as recited in claim 20 in which the ultrasonic transducer is comprised of an array of transducer elements and the focused ultrasound energy is moved electronically.

24. The method as recited in claim 19 in which the ultrasonic transducer produces two ultrasonic beams that differ in frequency by a beat frequency.

25. The method as recited in claim 24 in which the selected acoustic force frequency is equal to the beat frequency.

26. The method as recited in claim 19 in which the ultrasonic transducer produces an amplitude-modulated beam in which the frequency of the amplitude modulation results in a modulation frequency.

27. The method as recited in claim 26 in which the selected acoustic force frequency is proportional to the modulation frequency.

28. The method as recited in claim 19 in which step e) includes estimating a surface reflection coefficient at locations on the surface of the object and compensating for variations in the surface reflection coefficient over the surface of the object.

29. The method as recited in claim 1 in which the ultrasonic transducer is comprised of an array of transducer elements and the acoustic force is moved electronically.

30. The method as recited in claim 19 in which the ultrasonic transducer is comprised of an array of transducer elements and the acoustic force is moved electronically.

31. The method as recited in claim 19 in which step d) includes
   i) positioning the ultrasonic transducer in spaced relationship over the surface of the object such that a focal point of the ultrasonic transducer is positioned at a selected distance below the surface of the object;
   ii) operating the ultrasonic transducer to apply an acoustic force to the focal point at a selected acoustic force frequency;
   iii) sensing an acoustic emission field produced by the object in response to the acoustic force applied in step ii);
   iv) repeating steps i)-iii) while incrementally moving the focal point of the ultrasonic transducer along a direction perpendicular to the surface of the object until the focal point is positioned at the selected distance above the surface of the object; and
   v) storing the acoustic emission fields sensed in step iii) as the calibration signal.

32. The method as recited in claim 19 in which step e) includes amplifying the acoustic emission field sensed in step c) by an inverse of the calibration signal provided in step d).

* * * * *